United States Patent [19]
Hirose et al.

[11] Patent Number: 5,149,521
[45] Date of Patent: Sep. 22, 1992

[54] COMPOSITION FOR USE IN ORAL CAVITY

[75] Inventors: Kazuko Hirose, Tokyo; Kouji Maeda, Utsunomiya; Kenichi Arai, Takasaki; Takeshi Inoue, Utsunomiya, all of Japan

[73] Assignee: Kao Corporation, Tokyo, Japan

[21] Appl. No.: 751,084

[22] Filed: Aug. 28, 1991

[30] Foreign Application Priority Data

Aug. 31, 1990 [JP] Japan ................... 2-229876
Dec. 10, 1990 [JP] Japan ................... 2-407182

[51] Int. Cl.$^5$ .................. A61K 7/16; A61K 7/26; A61K 9/68
[52] U.S. Cl. ........................ 424/58; 424/48; 424/49; 424/440
[58] Field of Search ...................... 424/48-58

[56] References Cited

U.S. PATENT DOCUMENTS

| | | | |
|---|---|---|---|
| 3,767,791 | 10/1973 | Cordon et al. | 424/49 |
| 4,201,794 | 5/1980 | Sumitani | 426/96 |
| 4,469,673 | 9/1984 | Hoka et al. | 424/58 |
| 4,490,407 | 12/1984 | Lafon | 427/2 |
| 4,687,662 | 8/1987 | Schobel | 514/960 |
| 4,911,952 | 3/1990 | Doane et al. | 514/965 |
| 4,948,615 | 8/1990 | Zallie et al. | 426/578 |
| 5,055,461 | 10/1991 | Kelleher et al. | 514/688 |

FOREIGN PATENT DOCUMENTS

| | | | |
|---|---|---|---|
| 146308 | 6/1985 | European Pat. Off. | 424/58 |
| 252374 | 1/1988 | European Pat. Off. | 424/58 |
| 265386 | 4/1988 | European Pat. Off. | 424/58 |
| 0448895 | 10/1991 | European Pat. Off. | |
| 59-163307 | 9/1984 | Japan | 424/58 |
| 1166628 | 10/1969 | United Kingdom | |
| 2169788 | 7/1986 | United Kingdom | 424/58 |

OTHER PUBLICATIONS

Chemical Abstracts, vol. 101, 1984, p. 297, item 235403b.
Noller, Chemistry of Organic Compounds, 1951, p. 773.

*Primary Examiner*—Shep K. Rose
*Attorney, Agent, or Firm*—Oblon, Spivak, McClelland, Maier & Neustadt

[57] ABSTRACT

A composition for use in the oral cavity comprising (A) an easily breakable granule, (B) menthol and/or a natural substance containing menthol, and (C) a flavoring component such as basil, laurel, lavender or a lactone. Although the composition contains an easily breakable granule, which causes a powdery sensation characteristic of compositions containing granules, the present composition exhibits a greatly reduced powdery feeling, and gives a pleasant feeling to users. The composition is particularly suitable as a dentifrice.

8 Claims, No Drawings

COMPOSITION FOR USE IN ORAL CAVITY

BACKGROUND OF THE INVENTION

1. Field of the Invention

This invention relates to a composition for use in the oral cavity, and more particularly to a composition for use in the oral cavity comprising an easily breakable granule, capable of giving a pleasant feeling to users.

2. Description of the Background Art

In order to impart an abrading property, various granules have been incorporated into compositions for use in the oral cavity, such as a tooth paste and a tooth powder. For example, the granule disclosed in Japanese Patent Publication No. 53-7570 is prepared by using a water-insoluble abrading agent suitable for use in a dentifrice, and an agglomerating agent by means of a dry- or wet-type granulation method. Further examples include a macroscopic agglomerate of finely divided particles of an abrading agent, ground with a water-insoluble binder, as disclosed in Japanese Laid-Open Patent Application No. 48-13558; a granule as disclosed in Japanese Laid-Open Patent Application No. 58-126806, comprising ethyl cellulose, which is insoluble in water but soluble in ethanol, and a water-insoluble powder; a granule as disclosed in Japanese Laid-Open Patent Application No. 63-130522, which is prepared by mixing a granular material containing a powder which is substantially insoluble in water and a water-soluble polymer having a functional group which is reactive with a polyvalent metal ion, and treating the mixture with the polyvalent metal ion; a granule as disclosed in Japanese Laid-Open Patent Application No. 63-250313, which contains as essential components magnesium aluminate metasilicate and polyphosphate; and a granule as disclosed in Japanese Laid-Open Patent Application No. 1-299211, which is prepared by binding a water-insoluble powder with a water-insoluble inorganic binder, and which can pass through a 30-mesh sieve but cannot pass through a 200-mesh sieve, and is breakable under a pressure resulting from a load of 0.1 to 10 g per particle thereof.

The present composition for use in the oral cavity is required to give a pleasant feeling to users. For this reason, prior compositions generally incorporated a flavoring material, such as menthol or a natural substance containing menthol, into the composition.

However, the present inventors have found that a composition for use in the oral cavity containing an easily breakable granule gives a powdery feeling to users when it contains a flavoring material consisting of menthol or a natural substance containing menthol.

Thus, there is a demand for a composition for use in the oral cavity containing an easily breakable granule, which does not result in a powdery sensation when used, but rather, gives a pleasant feeling to users.

SUMMARY OF THE INVENTION

Accordingly, it is an object of the present invention to provide a composition for use in the oral cavity which reduces the powdery sensation caused by compositions containing an easily breakable granule and, as a flavoring material, only menthol or a natural substance containing menthol.

It is a further object of the present invention to provide a composition for use in the oral cavity which imparts a pleasant feeling to users.

It is a further object of the present invention to provide a composition for use in the oral cavity which has a sufficient abrading property.

These and other objects which will become apparent during the course of the following detailed description of the present invention have been realized by a composition for use in the oral cavity comprising (A) an easily breakable granule, (B) one or more flavoring components selected from the group consisting of menthol and natural substances containing menthol, and (C) one or more flavoring components selected from the group consisting of essential oils and extracts of basil, camphor, caraway, cardamom, coriander, geranium, ginger, laurel, lavender, mace, nutmeg, pepper, rose, rosemary, thyme, ylang ylang, jasmin, vanilla, hyssop, lavandin, orris, carrot seed, davana, elemi and osmanthus; borneol and its derivatives; heliotropin, $\alpha$-ionone, $\beta$-ionone, $\gamma$-ionone, $\delta$-ionone and derivatives thereof; lactones; and thymol, vanillin, ethyl vanillin, maltol and ethyl maltol.

DETAILED DESCRIPTION OF THE INVENTION PREFERRED EMBODIMENTS

Component (A) of the present invention is an easily breakable granule, which keeps its granular shape in the composition, but is deformed or broken when the composition is used in the mouth. It is preferable that the easily breakable granule have mechanical properties such that the granule, once immersed in water, is deformed or broken when pressed between two parallel plates bearing a load of from 0.01 to 50 g, more preferably from 0.1 to 10 g, per granule.

The easily breakable granule is prepared by a conventional granulation method using one or more of the following starting materials:

(1) Water-insoluble powdery materials which are conventionally used as abrading agents or coloring agents dentifrices;
(2) Conventional shaping agents and/or binding agents;
(3) Oils, fats, polymers which are insoluble in water and soluble in another solvent, and/or polymers which becomes water-insoluble when a polyvalent metal is reacted therewith;
(4) Thermoplastic and/or thermosetting resins which are conventionally used in adhesives; and
(5) Pharmaceutical agents and/or flavoring components which are generally used in dentifrices.

Examples of water-insoluble powdery materials suitable for use in the present component (A) include calcium secondary phosphate, calcium tertiary phosphate, insoluble sodium metaphosphate, silica, aluminum hydroxide, magnesium phosphate, calcium carbonate, calcium pyrophosphate, zeolites, composite aluminosilicate, magnesium carbonate, red iron oxide and calcium sulfate. Preferably, at least one of the suitable examples of the water-insoluble powdery material is employed in the present composition.

Examples of shaping and binding agents in the present component (A) include colloidal silica, magnesium aluminate metasilicate, bentonite, montmorillonite, kaolin, synthetic aluminosilicates, calcium silicate, aluminum hydroxide gel, aluminum sol, magnesium carbonate, synthetic hydrotalcite, magnesium oxide and magnesium hydroxide.

Examples of oils and fats suitable for use in the present component (A) include higher fatty acids and derivatives thereof, such as waxes, paraffins, stearic acid, lauric acid, myristic acid, palmitic acid, oleic acid, linoleic acid, linolenic acid, eleostearic acid, and esters and salts thereof, such as lower alkyl esters, higher alkyl ($C_6$–$C_{22}$) esters, hydroxy(lower alkyl) esters, and ammonium salts, lithium salts, sodium salts, potassium salts, zinc salts, magnesium salts and calcium salts. A preferred fatty acid is stearic acid, and preferred salts are magnesium stearate and calcium stearate. Examples of the polymers which are insoluble in water and soluble in another solvent, or which become water-insoluble when reacted with a polyvalent metal include a homopolymer or copolymer of compounds such as acrylic acid, acrylate esters, methacrylic acid, methacrylate esters, hydroxymethacrylate esters, styrene, vinyl acetate, vinyl pyrrolidone, maleic acid esters, methyl vinyl ether and α-olefins, such as ethylene, propylene, 1-butylene, 1-pentene, 1-hexene, 1-octene, 1-decene, and 1-dodecene; methyl cellulose, carboxyethylhydroxyethyl cellulose, carrageenan, xanthan gum, guaiac gum, tragacanth (traganth) gum, alginates, acacia gum, gelatin, natural or modified starch and alkaline metal salts of carboxymethyl cellulose; and derivatives of polyethylene glycol.

Examples of the thermoplastic resins suitable for use in the present component (A) include emulsions of polymers and copolymers, such as polyvinyl acetate, polyurethanes, polyvinyl butyral, copolymers of vinyl acetate and one or more acrylate esters, copolymers of vinyl chloride and vinyl acetate, and copolymers of ethylene and vinyl acetate; aqueous solutions of compounds and polymers, such as gum arabic, casein, glue, gelatin, starch, dextrin, soybean protein, methyl cellulose, ethyl cellulose, hydroxyethyl cellulose, serum albumin, polyvinyl methyl ether, polyvinyl pyrrolidone and polyvinyl alcohol; hot melts such as copolymers of vinyl acetate and ethylene, copolymers of ethylene and acrylate esters, phenoxy resins, polyamides, nylon 11, nylon 12, copolymeric nylons, saturated polyesters, coumarone-indene resins, canadian balsam, shellac, rosin, oleoresins and waxes; instant adhesives, such as cyanoacrylates; solvent solutions of polymers such as polyvinyl acetate, copolymers of vinyl chloride and vinyl acetate, polyurethanes and polyvinyl butyral; and monomer cements, such as those of polystyrene, polymethyl methacrylate, polyvinyl chloride, polycarbonates, cellulose acetate and methyl methacrylate.

Examples of thermosetting resins suitable for use in the present component (A) include monomer cements of resins such as urea resins, melamine resins, condensation products of urea and melamine, phenol resins, resorcinol resins, furan resins, copolymeric resins of α-olefins (such as those described above) and maleic anhydride, and aqueous vinyl urethane resins; epoxy resins; unsaturated polyesters; thermosetting acrylic resins such as diacrylates, dimethacrylates, urethane diacrylates and modified acrylic resins; polyaromatic resins such as polyamides, polyamideimides and polybenzimidazoles; and polymer-alloy-type resins such as phenolic-epoxy resins, phenolic-polyvinyl butyral, phenolic-polyvinyl formal, phenolic-nitrile rubbers, phenolic-nylons, epoxy-urethanes, epoxy resins, epoxy-nitrile rubbers, polyester epoxy resins, phenolic-chloroprenes and epoxy-silicones.

In addition to the above, rubber latexes such as natural rubbers, polyisobutylene rubbers, regenerated rubbers, polybutadiene rubbers, styrene-butadiene rubbers, chloroprene rubbers, nitrile rubbers, butyl rubbers, urethane rubbers and silicone rubbers can be also employed in the present invention.

Examples of pharmaceutical agents suitable for use in the present component (A) include antiplasmin agents such as allantoin, epsilon aminocaproic acid and tranechisam acid; enzymes such as dextranase, amylase, protease, mutanase, lysozyme, bacteriolysis enzymes and lytic enzymes; anticaries agents, such as alkali metal salts of monofluorophosphoric acid, such as sodium monofluorophosphate and potassium monofluorophosphate; fluorides such as sodium fluoride, ammonium fluoride and stannous fluoride; polyol phosphoric acid compounds such as salts of chlorohexydine, quaternary ammonium salts, dehydrocholesterol, glycyrrhetinic acid and salts thereof; glycerophosphate; and tartar preventing agents such as chlorophyll, caropeptides, vitamins, sodium chloride, carbonates, organic acids, water-soluble inorganic acid compounds and zeolites.

The easily breakable granules for use in the present invention can be prepared by any known method, such as rolling granulation, extruding granulation, compressing granulation, crushing granulation, stirring granulation, fluidized bed granulation, spray drying granulation and melting-solidifying granulation. Preferably, the easily breakable granules are prepared by one of the following methods;

(a) the granulation method disclosed in Japanese Laid-Open Patent Application No. 1-299211, in which an inorganic powder is combined with an inorganic binder, then is granulated by means of spray drying; and (b) the granulation method disclosed in Japanese Laid-Open Patent Applications No. 63-130522, No. 63-250313 and No. 58-126806, in which an inorganic powder is combined with an organic binder, then is granulated by means of spray drying.

The weight-average particle size of the easily breakable granule is preferably in the range of from 10 μm to 2 mm, more preferably from 75 μm to 500 μm. When the granule has a weight-average particle size of less than 10 μm, it cannot fulfill its abrading function satisfactorily. On the other hand, when the granule has a weight-average particle size of more than 2 mm, the resulting composition tends to give an unpleasant feeling to users.

It is preferable that the particle shape of the easily breakable granule be spherical, but even those granules whose particle shapes are not spherical are also suitable for use in the present composition.

No particular limitation is imposed on the amount of the easily breakable granule incorporated in the present composition. However, the preferred amount of the granule in the present composition is from 1 to 50 wt. %, more preferably from 3 to 30 wt. %, and most preferably from 10 to 20 wt. % of the total weight of the composition. When the amount of the granule is less than 1 wt. %, the abrading effects of the present composition may not be satisfactorily obtained. On the other hand, when the amount of the granule is in excess of 50 wt. %, the resulting composition tends to give an unpleasant feeling to users.

Examples of natural substances containing menthol suitable for use as the present component (B), include peppermint oil, Japanese mint, and spearmint. The natural substances containing menthol are isolated from natural sources, and may contain one or more additional components, in addition to menthol, such as tannin, carvone, and the like.

Examples of lactones suitable for use as component (C) include lactones having a five-, six- or seven-membered lactone ring such as δ-octalactone, δ-nonalactone, δ-decalactone, δ-undecalactone, δ-dodecalactone, δ-octalactone, δ-nonalactone, δ-decalactone, δ-undecalactone, δ-dodecalactone, ε-decalactone and ε-dodecalactone.

Any stereochemical form of borneol is suitable for use as component (C) in the present composition, such as d-borneol, l-borneol or dl-borneol. Suitable derivatives of borneol include bornyl halides, such as bornyl fluoride, bornyl chloride, boryl bormide and boryl iodide, and bornyl esters, such as bornyl acetate, bornyl propionate, bornyl butyrate, and bornyl salicylate.

Suitable derivatives of α-, β-, γ- and δ-ionone include conventional derivatives of ketones, such as imines, formed from reaction with a primary amine, with concomitant loss of water; oximes formed from an O-substituted hydroxylamine, with concomitant loss of water; a semicarbazide, formed from reaction with semicarbazone ($H_2NC(=O)NHNH_2$) or its hydrochloride salt, with concomitant loss of water; and a hydrozide, which may be substituted with a lower alkyl group, a phenyl group, a tolyl group, a benzyl group, and the like.

The component (B), the component (C) and other flavoring materials are hereinafter referred to collectively as a "flavoring composition". It is preferable that the amount of the flavoring composition incorporated into the present composition for use in the oral cavity be in the range of 0.1 to 10 wt. % of the total weight of the composition for use in the oral cavity, preferably form 0.3 to 5 wt. %, most preferably from 0.5 to 3 wt. %. Furthermore, the amount of the component (C) present in the flavoring composition is preferably from 1 ppm to 10 wt. %, preferably from 3 ppm to 5 wt. %, most preferably from 5 ppm to 1 wt. %. Examples of additional flavoring materials suitable for use in the flavoring composition other than those recited for components (B) and (C) include 1-carvone, anethole, cineol, methyl salicylate, eugenol, cinnamon oil, anise oil, cassia oil, lemon oil and orange oil. These flavoring materials can be used either alone or in mixtures thereof.

In addition to the above-described essential components (A), (B) and (C), other suitable components such an abrading agents, binding agents, stickiness-imparting agents, surface active agents, sweetening agents, antiseptic agents, and other effective components may be incorporated into the composition of the present invention.

The composition for use in the oral cavity according to the present invention can be used as, for instance, a dentifrice such as a tooth paste, a moistened dentifrice and a liquid dentifrice, a mouth washing agent, a troche, a chewing gum, a paste for the mouth, a massage cream for gingiva, a liquid mouth refreshing agent and a solid mouth refreshing agent.

Although the easily breakable granule of the present composition typically results in a powdery feeling when used, the present composition does not result in a powdery sensation when used in the oral cavity. Furthermore, the present composition gives a pleasant feeling to users.

This invention will now be explained more specifically with reference to the following Referential Examples (preparation examples of the component (A)) and Composition Examples, which are given for illustration of this invention and are not intended to be limiting thereof.

REFERENTIAL EXAMPLE 1

An aqueous slurry (water content: approximately 60 wt. %) containing, as water-insoluble powdery materials, 60 parts by weight of a zeolite (4A, 99.9 wt. % of which has a particle size of 10 μm or less type particles; average particle size: 2 μm), 10 parts by weight of silicic anhydride (colloidal silica) and 30 parts by weight of magnesium aluminate metasilicate was prepared. The slurry was granulated by spray drying, using a spray drying granulation machine.

The granule thus obtained passed through a 30-mesh sieve, but did not pass through a 200-mesh sieve, and was breakable under the pressure resulting from a load of 0.1 to 10 g per granule.

REFERENTIAL EXAMPLE 2

40 parts by weight of zeolite, 3 parts by weight of titanium oxide, 15 parts titanium oxide, 15 parts by weight of magnesium metasilicate and 2 parts by weight of ammonium carboxymethyl cellulose were kneaded with water to give a slurry. The slurry was subjected to spray drying granulation, thereby obtaining a granule. The granule was immersed in a 0.5 wt. % aqueous solution of zinc chloride for 10 minutes, and then collected by filtration. After washing with water, the granule was dried at a temperature of 70° C. The granule thus obtained was not easily broken even when it was placed in water and the mixture was agitated violently.

REFERENTIAL EXAMPLE 3

A slurry consisting of 80 wt. % of magnesium aluminate metasilicate and 20 wt. % of purified water, and a slurry consisting of 20 wt. % of sodium pyrophosphate and 80 wt. % of purified water were respectively prepared. These two slurries were uniformly mixed, and the resulting mixture was granulated by spray drying, using a spray drying apparatus of which the entrance temperature was maintained at 250° C.

REFERENTIAL EXAMPLE 4

5 parts by weight of powdery ethyl cellulose (10 cps) was dissolved in 5 parts by weight of ethanol (95%). The resulting solution was mixed with 95 parts by weight of calcined alumina having a particle size of 0.5 to 10 microns and an average particle size of 3 to 5 microns (MICRONOLIT WCA 9F, trademark) by use of a Hobart mixer for approximately 4 minutes, thereby obtaining a uniform mixture. The mixture was passed through a No. 10 sieve (U.S. Sieve Standard), and the extruded mixture was then dried in an oven at a temperature of 65° C. for one hour. Subsequently, the dried mixture was sifted with a No. 30 sieve, then a No. 60 sieve. Finally, the granules consisting of the calcined alumina and the ethyl cellulose remaining on the No. 60 sieve were collected.

REFERENTIAL EXAMPLE 5

20 parts by weight of a polyethylene fine powder binder (non-emulsifying grade, having a softening point of approximately 102° C. and an average molecular weight of approximately 1500), 80 parts by weight of finely divided particles of zirconium silicate (having an average particle diameter of 1 micron and a Mohs hardness number of 8), and one part by weight of an aluminum lake pigment (FD & C Red No. 2) were mixed in a proper vessel by means of a dry process. The vessel was placed in a heating apparatus, and the mixture in the vessel was stirred while heating the vessel. When the temperature of the mixture reached the softening point of the polyethylene binder, the vessel was taken out from the heating apparatus before the binder began to melt. The mixture was stirred while cooling. The cooled mixture was ground with a kneader to obtain finely divided particles, followed by sifting with a 40-mesh sieve, then a 60-mesh sieve. Granules which passed through the 40-mesh sieve but remained on the 60-mesh sieve were vivid red in color, and had an average particle size between approximately 250 microns and 420 microns.

REFERENTIAL EXAMPLE 6

220 parts by weight of dicalcium phosphate dihydrate having an average particle size of approximately 4.2 microns were mixed with 91 parts by weight of a 10% aqueous solution of acacia rubber in a Hobart mixer, thereby obtaining a uniformly moistened mixture. The mixture was forced through a sieve having a uniform mesh of 2380 microns, then was dried in an oven at a temperature of 65° C. for one hour. The dried, agglomerated mixture was sifted using a sieve having a uniform mesh of 420 microns. As a result, 132 parts by weight of agglomerated dicalcium phosphate dihydrate remained on a sieve having a uniform mesh of 840 microns, and 37 parts by weight agglomerated dicalcium phosphate dihydrate passed through the sieve having a uniform mesh of 420 microns.

COMPOSITION EXAMPLE 1

A series of tooth pastes having the formulation shown in Table 1, using the easily breakable granule obtained in Referential Example 1, were respectively prepared with each of the flavoring compositions containing the flavoring components (B) shown in Table 2, each of which were combined with the flavoring components (C) shown in Tables 3 and 4.

TABLE 1

| Formulation of Tooth Paste | |
|---|---|
| | parts by weight |
| Granule obtained in Referential Example 1 | 15.0 |
| Glycerin | 10.0 |
| Sorbitol | 30.0 |
| Carrageenan | 2.0 |
| Sodium laurylsulfate | 1.2 |
| Sodium saccharide | 0.1 |
| Methylparaben | 0.1 |
| Flavoring composition | 0.8 |
| Purified water | balance |
| | 100 |

TABLE 2

| Flavoring Component (B) (wt. %) | B-1 | B-2 |
|---|---|---|
| Peppermint oil | 50 | 20 |
| Menthol | 40 | 35 |
| Spearmint oil | 4 | 30 |
| Carvone | 3 | 10 |
| Anethole | 3 | 5 |
| Total | 100 | 100 |

The above-obtained tooth pastes were evaluated in terms of a reduced powdery feeling in accordance with the Standard Evaluation described below. The results are shown in Tables 3 and 4 below.

Comparative tooth pastes were also prepared by using the easily breakable granule obtained in Referential Example 1 and each of the flavoring components (C) shown in Table 5, without using a flavoring component (B). Each of the comparative tooth pastes were evaluated using the Standard Evaluation described below. The results of the comparative tests are shown in Table 5.

Standard Evaluation of Powdery Feeling

A tooth paste containing only component (B) as a flavoring component was employed as the reference composition, then the powdery feeling resulting from the use thereof was compared to the feeling resulting from use of the composition of the present invention. The results shown in Table 5 were obtained by using a tooth paste containing no flavoring component, then comparing the powdery feeling resulting thereof to the feeling resulting from use of the composition containing only component (C) as the flavoring component.

⦿: Remarkably reduced
◉: Reduced
Δ: Slightly reduced
X: Not reduced

TABLE 3

| Component (C) | Proportion of Component (C) to Flavoring Component B-1 (wt. %) | Amount of Flavoring Composition in Tooth Paste (wt. %) | Powdery Feeling |
|---|---|---|---|
| — | 0 (Component B-1 only) | 0.8 | X |
| Laurel oil | 0.1 | 0.8 | ○ |
| Camphor oil | 0.1 | 0.8 | ○ |
| Pepper oleoresin | 0.01 | 0.8 | ◉ |
| Ginger oleoresin | 0.01 | 0.8 | ◉ |
| Ginger oil | 0.01 | 0.8 | ○ |
| Thyme oil | 0.01 | 0.8 | ◉ |
| Rose oil | 0.001 | 0.8 | ○ |
| Rose absolute | 0.001 | 0.8 | ○ |
| d-Borneol | 0.001 | 0.8 | Δ |
| γ-Undecalactone | 0.001 | 0.8 | ○ |
| Vanillin | 0.01 | 0.8 | ○ |

TABLE 4

| Component (C) | Proportion of Component (C) to Flavoring Component B-2 (wt. %) | Amount of Flavoring Composition in Tooth Paste (wt. %) | Powdery Feeling |
|---|---|---|---|
| — | 0 (Component B-2 only) | 0.8 | X |
| Laurel oil | 0.1 | 0.8 | ○ |
| Camphor oil | 0.1 | 0.8 | ○ |
| Pepper oleoresin | 0.01 | 0.8 | ◉ |
| Ginger oleoresin | 0.01 | 0.8 | ◉ |
| Ginger oil | 0.01 | 0.8 | ○ |
| Thyme oil | 0.01 | 0.8 | ◉ |
| Rose oil | 0.001 | 0.8 | ○ |
| Rose absolute | 0.001 | 0.8 | ○ |
| d-Borneol | 0.001 | 0.8 | Δ |
| γ-Undecalactone | 0.001 | 0.8 | ○ |
| Vanillin | 0.01 | 0.8 | ○ |

TABLE 5

| Component (C) | Amount of Flavoring Component (C) in Tooth Paste* (wt. %) | Powdery Feeling |
|---|---|---|
| Laurel oil | 0.1 | X |
| Camphor oil | 0.1 | X |
| Pepper oleoresin | 0.1 | X |
| Thyme oil | 0.1 | X |
| Rose oil | 0.1 | X |
| d-Borneol | 0.1 | X |

TABLE 5-continued

| Component (C) | Amount of Flavoring Component (C) in Tooth Paste* (wt. %) | Powdery Feeling |
|---|---|---|
| Vanillin | 0.1 | X |

Note:
Tooth paste composition contains no flavoring component (B)

As is clear from the data shown in Tables 3 and 4, the powdery feeling is reduced by incorporating component (C) into a tooth paste which comprises an easily breakable granule, and menthol or a natural substance containing menthol as the main flavoring component.

It is also seen from the data shown in Table 5 that the powdery feeling is not reduced by incorporation of component (C) into a tooth paste if the tooth paste does not contain menthol or a natural substance containing menthol as a flavoring component.

EXAMPLE 2

A tooth paste having the following formulation was prepared by using the easily breakable granule obtained in Referential Example 2 and the flavoring component B-1 shown in Table 2.

| Formulation of Tooth Paste: | parts by weight |
|---|---|
| Granule obtained in Referential Example 2 | 15.0 |
| Glycerin | 10.0 |
| Sorbitol | 30.0 |
| Carrageenan | 2.0 |
| Sodium laurylsulfate | 1.2 |
| Sodium saccharide | 0.1 |
| Methylparaben | 0.1 |
| Flavoring Component B-1 | 0.5 |
| Camphor oil | 0.001 |
| Ginger oleoresin | 0.0001 |
| Purified water | balance |
| | 100 |

EXAMPLE 3

A tooth paste having the following formulation was prepared by using the easily breakable granule obtained in Referential Example 3 and the flavoring component B-1 shown in Table 2.

| Formulation of Tooth Paste: | parts by weight |
|---|---|
| Granule obtained in Referential Example 3 | 15.0 |
| Glycerin | 10.0 |
| Sorbitol | 30.0 |
| Carrageenan | 2.0 |
| Sodium laurylsulfate | 1.2 |
| Sodium saccharide | 0.1 |
| Methylparaben | 0.1 |
| Flavoring Component B-1 | 0.8 |
| Cardamon oil | 0.001 |
| Thyme oil | 0.0001 |
| α-Ionone | 0.00001 |
| Purified water | balance |
| | 100 |

EXAMPLE 4

A tooth paste having the following formulation was prepared by using the easily breakable granule obtained in Referential Example 4 and the flavoring component B-1 shown in Table 2.

| Formulation of Tooth Paste: | parts by weight |
|---|---|
| Granule obtained in Referential Example 4 | 15.0 |
| Glycerin | 10.0 |
| Sorbitol | 30.0 |
| Carrageenan | 2.0 |
| Sodium laurylsulfate | 1.2 |
| Sodium saccharide | 0.1 |
| Methylparaben | 0.1 |
| Flavoring Component B-1 | 0.7 |
| Caraway oil | 0.0001 |
| Pepper oleoresin | 0.00001 |
| d-Borneol | 0.00001 |
| Purified water | balance |
| | 100 |

EXAMPLE 5

A tooth paste having the following formulation was prepared using the easily breakable granule obtained in Referential Example 5 and the flavoring component B-2 shown in Table 2.

| Formulation of Tooth Paste: | parts by weight |
|---|---|
| Granule obtained in Referential Example 5 | 15.0 |
| Glycerin | 10.0 |
| Sorbitol | 30.0 |
| Carrageenan | 2.0 |
| Sodium laurylsulfate | 1.2 |
| Sodium saccharide | 0.1 |
| Methylparaben | 0.1 |
| Flavoring Component B-2 | 0.8 |
| Basil oil | 0.001 |
| Ginger oil | 0.0001 |
| Rosemary oil | 0.0001 |
| Purified water | balance |
| | 100 |

EXAMPLE 6

A tooth paste having the following formulation was prepared by using the easily breakable granule obtained in Referential Example 6 and the flavoring component B-2 shown in Table 2.

| Formulation of Tooth Paste: | parts by weight |
|---|---|
| Granule obtained in Referential Example 6 | 15.0 |
| Glycerin | 10.0 |
| Sorbitol | 30.0 |
| Carrageenan | 2.0 |
| Sodium laurylsulfate | 1.2 |
| Sodium saccharide | 0.1 |
| Methylparaben | 0.1 |
| Flavoring Component B-2 | 0.7 |
| Rose oil | 0.00001 |
| Heliotropin | 0.00001 |
| Pepper oil | 0.0001 |
| Purified water | balance |
| | 100 |

Use of the tooth pastes obtained in Examples 2 to 6 did not result in a powdery feeling, and gave a pleasant feeling to users.

What is claimed as new and desired to be secured by Letters Patent of the United States is:

1. A pharmaceutical composition for treatment in the oral cavity comprising:
   (A) an abrasive water-insoluble granule having a weight-average particle size of 10 μm to 2 mm, which is easily breakable or deformable when used in the oral cavity.
   (B) menthol or a naturally occurring substance comprising menthol and at least one additional component, as a flavoring component,
   (C) one or more additional flavoring components selected from the group consisting of oils and extracts of basil, camphor, caraway, cardamon, coriander, geranium, ginger, laurel, lavender, mace, nutmeg, peper, rose, rosemary, thyme, ylang ylang, jasmin, vanilla, hyssop, lavandin, orris, carrot seed, davana, elemi and osmanthus, borneol and its derivatives; heliotropin, α-ionone, β-ionone, γ-ionone, δ-ionone and derivatives thereof; lactones; and thymol, vanillin, ethyl vanillin, maltol and ethyl maltol, and
   (D) a pharmaceutically acceptable carrier,
wherein said easily breakable or deformable granule (A) is present in an amount of from 1 to 50 wt. % of the total weight of said composition, said flavoring components (B) and (C) are present in a combined amount of from 0.1 to 10 wt. % of the total weight of said composition, and said flavoring component (C) is present in an amount of from 1 ppm to 10 wt. % of the total weight of said flavoring components (B) and (C).

2. A pharmaceutical composition for treatment in the oral cavity according to claim 1, wherein said easily breakable or deformable granule, once immersed in water, is deformed or broken when placed between two parallel plates and subjected to a pressure resulting from a load of from 0.01 to 50 g per granule.

3. A composition for use in the oral cavity according to claim 1, wherein said component (B) is a naturally occurring substance, comprising menthol and at least one additional component.

4. The composition for use in the oral cavity according to claim 3, wherein said naturally occurring substance is selected from the group consisting of peppermint oil, Japanese mint, and spearmint oil.

5. A composition according to claim 1 which is a tooth paste, a moistened dentifrice, a liquid dentifrice, a mouth washing agent, a troche, a chewing gum, a paste for the mouth, a massage cream for gingiva, a liquid mouth refreshing agent or a solid mouth refreshing agent.

6. A composition according to claim 1 which is a toothpaste.

7. A composition according to claim 1 which is a mouth washing agent.

8. A composition according to claim 1 which is a paste for the mouth.

* * * * *

UNITED STATES PATENT AND TRADEMARK OFFICE
CERTIFICATE OF CORRECTION

PATENT NO.   : 5,149,521
DATED        : September 22, 1992
INVENTOR(S)  : Kazuko Hirose, et. al.

It is certified that error appears in the above-indentified patent and that said Letters Patent is hereby corrected as shown below:

Column 11, line 16, delete "peper", insert --pepper--.

Signed and Sealed this

Ninth Day of November, 1993

Attest:

BRUCE LEHMAN

*Attesting Officer*　　　　　*Commissioner of Patents and Trademarks*